US010869476B2

(12) United States Patent
Dahmen et al.

(10) Patent No.: US 10,869,476 B2
(45) Date of Patent: Dec. 22, 2020

(54) USE OF PYDIFLUMETOFEN FOR THE REDUCTION OF MYCOTOXIN CONTAMINATION IN PLANTS

(71) Applicant: BAYER CROPSCIENCE AKTIENGESELLSCHAFT, Monheim am Rhein (DE)

(72) Inventors: Peter Dahmen, Neuss (DE); Pierre-Yves Coqueron, Lyons (FR); Ingo Wetcholowsky, Langenfeld (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/766,726

(22) PCT Filed: Oct. 7, 2016

(86) PCT No.: PCT/EP2016/074109
§ 371 (c)(1),
(2) Date: Apr. 6, 2018

(87) PCT Pub. No.: WO2017/060499
PCT Pub. Date: Apr. 13, 2017

(65) Prior Publication Data
US 2018/0279616 A1 Oct. 4, 2018

(30) Foreign Application Priority Data
Oct. 9, 2015 (EP) .................................... 15189239

(51) Int. Cl.
*A01N 43/56* (2006.01)
*C07D 233/56* (2006.01)
*A01C 1/06* (2006.01)

(52) U.S. Cl.
CPC ........... *A01N 43/56* (2013.01); *C07D 233/56* (2013.01); *A01C 1/06* (2013.01)

(58) Field of Classification Search
CPC ........ A01C 1/06; C07D 233/56; A01N 43/56; A01N 25/00
See application file for complete search history.

(56) References Cited

U.S. PATENT DOCUMENTS

| | | | | |
|---|---|---|---|---|
| 2009/0124678 | A1* | 5/2009 | Semar | A01N 43/653 514/383 |
| 2013/0237415 | A1* | 9/2013 | Doyle | A01N 25/32 504/105 |

FOREIGN PATENT DOCUMENTS

| | | | |
|---|---|---|---|
| WO | 2012021250 | A1 | 2/2012 |
| WO | 2013167651 | A1 | 11/2013 |
| WO | 2015124542 | A1 | 8/2015 |
| WO | 2015124543 | A1 | 8/2015 |

OTHER PUBLICATIONS

PubChem CID 56933411, National Center for Biotechnology Information. PubChem Compound Database; CID=56933411, https://pubchem.ncbi.nlm.nih.gov/compound/56933411 (accessed Jan. 23, 2019), create date Apr. 16, 2012 (Year: 2012).*
International Search Report of International Patent Application No. PCT/EP2016/074109 dated Nov. 8, 2016.

* cited by examiner

*Primary Examiner* — Yanzhi Zhang
(74) *Attorney, Agent, or Firm* — McBee Moore & Vanik IP, LLC

(57) ABSTRACT

The present invention relates to the novel use of the pyrazole carboxylic acid amide derivative Pydiflumetofen, compositions comprising this compound and its use in methods for the reduction of mycotoxin contamination in plants. Pydiflumetofen is also useful in increasing yield, in particular in cereals eg. wheat.

8 Claims, No Drawings

USE OF PYDIFLUMETOFEN FOR THE REDUCTION OF MYCOTOXIN CONTAMINATION IN PLANTS

CROSS-REFERENCE TO RELATED APPLICATIONS

This application is a National Stage entry of International Application No. PCT/EP2016/074109, filed 7 Oct. 2016, which claims priority to European Patent Application No. 15189239.5, filed 9 Oct. 2015.

FIELD OF THE INVENTION

The present invention relates to the novel use of the pyrazole carboxylic acid amide derivative Pydiflumetofen, compositions comprising this compound and its use in methods for the reduction of mycotoxin contamination in plants. Pydiflumetofen is also useful in increasing yield, in particular in cereals eg. wheat.

BACKGROUND OF THE INVENTION

Numerous fungi are serious pests of economically important agricultural crops. Further, crop contamination by fungal toxins is a major problem for agriculture throughout the world.

Mycotoxins, such as aflatoxins, ochratoxins, patulin, fumonisins, zearalenones, and trichothecenes, are toxic fungal metabolites, often found in agricultural products that are characterized by their ability to cause health problems for humans and vertebrates. They are produced for example by different *Fusarium* and *Aspergillus, Penicillium* und *Alternaria* species.

Aflatoxins are toxins produced by *Aspergillus* species that grow on several crops, in particular on maize or corn before and after harvest of the crop as well as during storage. The biosynthesis of aflatoxins involves a complex polyketide pathway starting with acetate and malonate. One important intermediate is sterigmatocystin and O-methylsterigmatocystin which are direct precursors of aflatoxins. Important producers of aflatoxins are *Aspergillus flavus*, most strains of *Aspergillus parasiticus, Aspergillus nomius, Aspergillus bombycis, Aspergillus pseudotamarii, Aspergillus ochraceoroseus, Aspergillus rambelli, Emericella astellata, Emericella venezuelensis, Bipolaris* spp., *Chaetomium* spp., *Farrowia* spp., and *Monocillium* spp., in particular *Aspergillus flavus* and *Aspergillus parasiticus* (Plant Breeding (1999), 118, pp 1-16). There are also additional *Aspergillus* species known. The group of aflatoxins consists of more than 20 different toxins, in particular aflatoxin B1, B2, G1 and G2, cyclopiazonic acid (CPA).

Ochratoxins are mycotoxins produced by some *Aspergillus* species and *Penicilium* species, like *A. ochraceus, A. carbonarius* or *P. viridicanum*, Examples for Ochratoxins are ochratoxin A, B, and C. Ochratoxin A is the most prevalent and relevant fungal toxin of this group.

Fumonisins are toxins produced by *Fusarium* (F.) species that grow on several crops, mainly corn, before and after harvest of the crop as well as during storage. The diseases, *Fusarium* kernel, ear and stalk rot of corn, is caused by *Fusarium verticillioides, F. subglutinans, F. moniliforme*, and *F. proliferatum*. The main mycotoxins of these species are the fumonisins, of which more than ten chemical forms have been isolated. Examples for fumonisins are FB1, FB2 and FB3. In addition the above mentioned *Fusarium* species of corn can also produce the mycotoxins moniliformin and beauvericin. In particular *Fusarium verticillioides* is mentioned as an important pathogen of corn, this *Fusarium* species produces as the main mycotoxin fumonisins of the B-type.

Trichothecenes are those mycotoxins of primary concern which can be found in *Fusarium* diseases of small grain cereals like wheat, barley, rye, triticale, rice, sorghum and oat. They are sesquiterpene epoxide mycotoxins produced by species of *Fusarium, Trichothecium*, and *Myrothecium* and act as potent inhibitors of eukaryotic protein synthesis.

Some of these trichothecene producing *Fusarium* species also infect corn/maize.

Examples of trichothecene mycotoxins include T-2 toxin, HT-2 toxin, isotrichodermol, DAS, 3-deacetylcalonectrin, 3,15-dideacetylcalonectrin, scirpentriol, neosolaniol; 15-acetyldeoxynivalenol, 3-acetyldeoxynivalenol, nivalenol, 4-acetylnivalenol (fusarenone-X), 4,15-diacetylnivalenol, 4,7,15-acetylnivalenol, and deoxynivalenol (hereinafter "DON") and their various acetylated derivatives. The most common trichothecene in *Fusarium* head blight is DON produced for example by *Fusarium graminearum* and *F. culmorum.*

Another mycotoxin mainly produced by *F. culmorum, F. graminearum* and *F. cerealis* is zearalenone, a phenolic resorcyclic acid lactone that is primarily an estrogenic fungal metabolite.

*Fusarium* species that produce mycotoxins, such as fumonisins and trichothecenes, include *F. acuminatum, F. crookwellense, F., verticillioides, F. culmorum, F. avenaceum, F. equiseti, F. moniliforme, F, graminearum* (*Gibberella zeae*), *F. lateritium, F. pose, F. sambucinum* (*G. pulicaris*), *F. proliferatum, F. subglutinans, F. sporotrichioides* and other *Fusarium* species.

Both acute and chronic mycotoxicoses in farm animals and in humans have been associated with consumption of wheat, rye, barley, oats, rice and maize contaminated with *Fusarium* species that produce trichothecene mycotoxins. Experiments with chemically pure trichothecenes at low dosage levels have reproduced many of the features observed in moldy grain toxicoses in animals, including anemia and immunosuppression, haemorrage, emesis and feed refusal. Historical and epidemiological data from human populations indicate an association between certain disease epidemics and consumption of grain infected with *Fusarium* species that produce trichothecenes. In particular, outbreaks of a fatal disease known as alimentary toxic aleukia, which has occurred in Russia since the nineteenth century, have been associated with consumption of overwintered grains contaminated with *Fusarium* species that produce the trichothecene T-2 toxin. In Japan, outbreaks of a similar disease called akakabi-byo or red mold disease have been associated with grain infected with *Fusarium* species that produce the trichothecene, DON. Trichothecenes were detected in the toxic grain samples responsible for recent human disease outbreaks in India and Japan. There exists, therefore, a need for agricultural methods for preventing, and crops having reduced levels of, mycotoxin contamination.

Further, mycotoxin-producing *Fusarium* species are destructive pathogens and attack a wide range of plant species. The acute phytotoxicity of mycotoxins and their occurrence in plant tissues also suggests that these mycotoxins play a role in the pathogenesis of *Fusarium* on plants. This implies that mycotoxins play a role in disease and, therefore, reducing their toxicity to the plant may also prevent or reduce disease in the plant. Further, reduction in disease levels may have the additional benefit of reducing mycotoxin contamination on the plant and particularly in grain where the plant is a cereal plant.

There is a need, therefore, to decrease the contamination by mycotoxins of plants and plant material before and/or after harvest and/or during storage.

Pydiflumetofen being a compound according the formula (I)

(I)

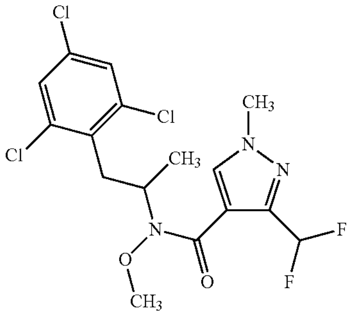

having the IUPAC name 3-(Difluoromethyl)-N-methoxy-1-methyl-N-[1-(2,4,6-trichlorophenyl)-2-propanyl]-1H-pyrazole-4-carboxamide and its production and use as a fungicide is described in WO-A 2010/063700. Related pyrazole-4-carboxylic acid amide derivatives and their use as for reducing mycotoxins are described in WO-A 2012/072575. Pydiflumetofen is described to have activity in the Sudden Death Syndrome described for corn in WO-A 2014/023628, a disease caused by certain *Fusarium* species.

The effect of fungicides on mycotoxin contamination in crops is discussed controversially as contradicting results are found. Disease development and mycotoxin production by the infecting fungi is influenced by a variety of factors not being limited to weather conditions, agricultural techniques, fungicide dose and application, growth stage of crops, colonization of crops by different fungi species, susceptibility of host crops and infection mode of fungi species. For example *Microdochium nivale* not producing any mycotoxin is able to reduce growth and DON accumulation of *F. culmorum*. It is also known that the different fungi use separate mutes when infecting the plant. For example *Fusarium* species producing fumonisins are known to infect maize by wound inoculation. The wounds are mainly caused by insects like the European and Southwestern corn borer or the corn earworm, in particular by the European corn borer (*Ostrinia nubialis*). Therefore it is discussed that maize being transformed with genes coding for insecticidal proteins for example with those from *Bacillus thuringiensis* should show reduced level of mycotoxins, in particular fumonisins (Wu, Transgenic Research (2006), 15, 277-289). In contrast other fungal species for example *Fusarium graminearum* and *Aspergillus flavus* are infecting maize via the silk channel. Also insect pest damage is less strongly correlated with aflatoxin concentrations in maize, because a variety of factors are influencing aflatoxin content in maize (Wu, Transgenic Research (2006), 15, 277-289).

Therefore prohibiting fungal infection via controlling insects that promote infection by wounding is not sufficient for reducing effectively mycotoxin contamination of maize, especially for DON. Zearalenone and aflatoxins.

It has also to be mentioned that breeding for fungal resistance in crops in contrast to insecticidal resistance is much more difficult. There have been several classical and transgenic breeding approaches, but obviously a high level of resistance is difficult to obtain.

Therefore application of fungicidal active compounds represents the most effective mode to control fungal infections of plants and thereby reducing mycotoxin content.

Therefore the problem to be solved by the present invention is to provide compounds which lead by their application on plants and/or plant material to a reduction in mycotoxins in all plant and plant material.

SUMMARY

Accordingly, the present invention provides a method of reducing mycotoxin contamination in plants and/or any plant material and/or plant propagation material comprising applying to the plant or plant propagation material an effective amount of Pydiflumetofen being a compound according the formula (I)

(I)

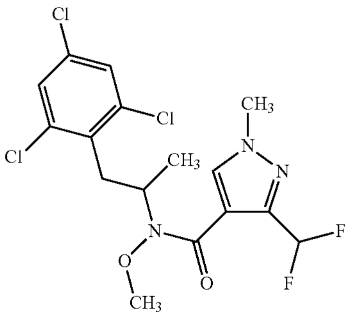

having the IUPAC name 3-(Difluoromethyl)-N-methoxy-1-methyl-N-[1-(2,4,6-trichlorophenyl)-2-propanyl]-1H-pyrazole-4-carboxamide;

or tautomers/isomers/enantiomers thereof.

The term Pydiflumetofen encompasses all tautomers, isomers or enantiomers of Pydiflumetofen.

DETAILED DESCRIPTION

As indicated above, it has now been found that Pydiflumetofen is useful in reducing mycotoxin contamination when it is applied to a plant and/or any plant material and/or plant propagation material in an effective amount.

In a particular embodiment Pydiflumetofen is useful in reducing mycotoxin contamination produced by fungi when applied to a plant and/or any plant material and/or plant propagation material in an effective amount.

In a particular embodiment Pydiflumetofen is useful for increasing yield when applied to a plant and/or any plant material and/or plant propagation material in an effective amount.

In a particular embodiment Pydiflumetofen is useful for increasing yield in cereals when applied to a plant and/or any plant material and/or plant propagation material in an effective amount.

In a particular embodiment Pydiflumetofen is useful for increasing yield in wheat when applied to a plant and/or any plant material and/or plant propagation material in an effective amount. The rates regarding Pydiflumetofen to achieve the yield increase are similar to those for reducing mycotoxins.

Pydiflumetofen is useful in reducing mycotoxin contamination when it is applied to a plant and/or any plant material and/or plant propagation material in an effective amount before and/or after harvest and/or during storage.

In a particular embodiment Pydiflumetofen is useful in reducing mycotoxin contamination produced by fungi selected from the group of the following species: *F. acuminatum, F. crookwellense, F. verticillioides, F. culmorum, F. avenaceum, F. equiseti, F. moniliforme, F. graminearum* (*Gibberella zeae*), *F. lateritium, F. poae, F. sambucinum* (*G. pulicaris*), *F. proliferatum, F. subglutinans* and *F. sporotrichioides, Aspergillus flavus*, most strains of *Aspergillus parasiticus* and *Aspergillus nomius, A. ochraceus, A. carbonarius* or *P. viridicatum* when applied to a plant and/or any plant material and/or plant propagation material in an effective amount.

In a particular embodiment Pydiflumetofen is useful in reducing mycotoxin contamination produced by fungi selected from the group of the following species: *F. verticillioides, F. culmorum, F. moniliforme, F. graminearum* (*Gibberella zeae*), *F. proliferatum, Aspergillus flavus*, most strains of *Aspergillus parasiticus* and *Aspergillus nomius, A. ochraceus, A. carbonarius* when applied to a plant and/or any plant material and/or plant propagation material in an effective amount.

In a particular embodiment Pydiflumetofen is useful in reducing mycotoxin contamination produced by fungi selected from the group of the following species: *F. verticillioides, F. proliferatum, F. graminearum* (*Gibberella zeae*), *Aspergillus flavus*, and *Aspergillus parasiticus* when applied to a plant and/or any plant material and/or plant propagation material in an effective amount.

In a particular embodiment Pydiflumetofen is useful in reducing mycotoxin contamination produced by fungi selected from the group of the following species: *F. verticillioides, F. proliferatum, F. graminearum* when applied to a plant and/or any plant material and/or plant propagation material in an effective amount.

In a particular embodiment Pydiflumetofen is useful in reducing mycotoxin contamination produced by fungi selected from the group of the following species: *Aspergillus flavus*, and *Aspergillus parasiticus* when applied to a plant and/or any plant material and/or plant propagation material in an effective amount.

In a particular embodiment the mycotoxins are selected from the following group: aflatoxins B1, B2, G1 and G2, ochratoxin A, B, C as well as T-2 toxin, HT-2 toxin, isotrichodermol, DAS, 3-deacetylcalonectrin, 3,15-dideacetylcalonectrin, scirpentriol, neosolaniol; zearalenone, 15-acetyldeoxynivalenol, nivalenol, 4-acetylnivalenol (fusarenone-X), 4,15-diacetylnivalenol, 4,7,15-acetylnivalenol, and deoxynivalenol (hereinafter "DON") and their various acetylated derivatives as well as fumonisins of the B-type as FB1, FB2, FB3.

In a very particular embodiment the mycotoxins are selected from the following group: aflatoxins B1, B2, G1 and G2, zearalenone, deoxynivalenol (hereinafter "DON") and their various acetylated derivatives as well as fumonisins of the B-type as FB1, FB2, FB3.

In a very particular embodiment the mycotoxins are selected from the following group: aflatoxins B1, B2, G1 and G2.

In a very particular embodiment the mycotoxins are selected from the following group: aflatoxins B1.

In a very particular embodiment the mycotoxins are selected from the following group: zearalenone, deoxynivalenol (hereinafter "DON") and their various acetylated derivatives.

In a very preferred particular embodiment the mycotoxin is deoxynivalenol (hereinafter "DON") and its various acetylated derivatives.

In a very particular embodiment the mycotoxins are selected from the following group: fumonisins of the B-type as FB1, FB2, FB3.

In a particular embodiment of the invention plant and/or plant material and/or plant propagation material has at least 10% less mycotoxin, more preferable at least 20% less mycotoxins, more preferable at least 40% less mycotoxins, more preferable at least 50% less mycotoxins more preferable at least 80% less mycotoxin contamination than plant or plant material which has not been treated.

In a particular embodiment of the invention plant and/or plant material and/or plant propagation material before and/or after harvest and/or during storage has at least 10% less mycotoxin, more preferable at least 20% less mycotoxins, more preferable at least 40% less mycotoxins, more preferable at least 50% less mycotoxins more preferable at least 80% less mycotoxin contamination than plant or plant material before and/or after harvest and/or during storage which has not been treated.

In a particular embodiment of the invention plant and/or plant material and/or plant propagation material before harvest has at least 10% less aflatoxins, more preferable at least 20% aflatoxin, more preferable at least 40% aflatoxins, more preferable at least 50% aflatoxins, more preferable at least 80% aflatoxin contamination than plant or plant material before harvest which has not been treated.

In a particular embodiment of the invention plant and/or plant material and/or plant propagation material after harvest has at least 10% less fumonisins, more preferable at least 20% fumonisins, more preferable at least 40% fumonisins, more preferable at least 50% fumonisins, more preferable at least 80% fumonisin contamination than plant or plant material after harvest which has not been treated.

In a particular embodiment of the invention plant and/or plant material and/or plant propagation material during storage has at least 10% less DON, more preferable at least 20% DON, more preferable at least 40% DON, more preferable at least 50% DON, more preferable at least 80% DON contamination than plant or plant during storage which has not been treated.

In a particular embodiment Pydiflumetofen can be combined with other active ingredients like fungicides, insecticides, herbicides, biological control agents.

In particular the fungicides are selected from the group comprising

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4- chlorophenoxy)-2-(trifluoromethyl)penyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl) butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl] methyl}-1H-1,2,4-triazol-5-yl thiocyanate, (1.041) 1-{[rel (2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylbeptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylbeptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylbeptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylbeptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylbeptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl) phenyl]-1-(1H-1,2,4-triazol-1-yl)propan-2-ol, (1.056) 2-{[3-(2-chlorophenyl)-2-(2,4-difluorophenyl)oxiran-2-yl] methyl}-2,4-dihydro-3H-1,2,4-triazole-3-thione, (1.057) 2-{[rel(2R,3R)-3-(2-chlorophenyl)-2-(2,4-difluorophenyl) oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl) cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl] methyl}-1H-1,2,4-triazole, (1.062) 5-(allylsulfanyl)-1-{[rel (2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl] sulfanyl}phenyl)-N-ethyl-N-methylimidoformamide, (1.067) N'-(2,5-dimethyl-4-{3-[(1,1,2,2-tetrafluoroethyl) sulfanyl]phenoxy}phenyl)-N-ethyl-N-methylimidoformamide, (1.068) N'-(2,5-dimethyl-4-{3-[(2,2,2-trifluoroethyl) sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl) ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide;

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030)

3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide;

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-(2-[(2,5-dimethylphenoxy)methyl]phenyl)-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide;

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine;

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram;

6) Compounds capable to induce a host defence, for example (6.001) acibenzolar-S-methyl, (6.002) isotianil, (6.003) probenazole, (6.004) tiadinil;

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinolone;

8) Inhibitors of the ATP production, for example (8.001) silthiofam;

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl) prop-2-en-1-one, (9.009) (2Z)-3-(4-tert-butylphenyl)-3-(2-chloropyridin-4-yl)-1-(morpholin-4-yl)prop-2-en-1-one;

10) Inhibitors of the lipid and membrane synthesis, for example (10.001) propamocarb, (10.002) propamocarb hydrochloride, (10.003) tolclofos-methyl;

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam);

13) Inhibitors of the signal transduction, for example (13.001) fludioxonil, (13.002) iprodione, (13.003) procymidone, (13.004) proquinazid, (13.005) quinoxyfen, (13.006) vinclozolin;

14) Compounds capable to act as an uncoupler, for example (14.001) fluazinam, (14.002) meptyldinocap;

15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) Oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7 (2H,6H)-tetrone, (15.035) 2-[3,5-bis(difluoromethyl)-1H-pyrazol-1-yl]-1-[4-(4-(5-[2-(prop-2-yn-1-yloxy)phenyl]-4,5-dihydro-1,2-oxazol-3-yl-1,3-thiazol-2-yl)piperidin-1-yl] ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl] ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl] ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl) quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl) oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl (6-[({[(1-methyl-1H-tetrazol-5-yl)(phenyl)methylene] amino}oxy)methyl]pyridin-2-yl}carbamate, All named mixing partners of the classes (1) to (15) can, if their functional groups enable this, optionally form salts with suitable bases or acids.

In one embodiment Pydiflumetofen can be combined with other active ingredients selected from the group comprising Prothioconazole, Tebuconazole, Metconazole, Difenconazole, Epoxiconazole, Trifloxystrobin, Azoxystrobin, Pyraclostrobin, Fluoxastrobin, Bixafen, Benzovindiflupyr, Fluopyram, Penflufen, Metalaxyl, Mefenoxam, Fenpropimorph and Thiophanate.

In another embodiment Pydiflumetofen can be combined with other active ingredients selected from the group comprising Prothioconazole, Tebuconazole, Metconazole, Difenconazole, Epoxiconazole, and Thiophanate.

The active ingredients specified above by their Common Name are known and described, for example, in The Pesticide Manual (16th Ed. British Crop Protection Council) or can be searched in the internet (e.g. www.alanwood.net/pesticides).

Where a fungicide compound as listed above can be present in tautomeric form, such a compound is understood herein above and herein below also to include, where applicable, corresponding tautomeric forms, even when these are not specifically mentioned in each case.

All named mixing partners of the classes (1) to (15) can, if their functional groups enable this, optionally form salts with suitable bases or acids.

According to the invention all plants and plant material can be treated. By plants is meant all plants and plant populations such as desirable and undesirable wild plants, cultivars (including naturally occurring cultivars) and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods including transgenic plants.

By plant material is meant all above ground and below ground parts and organs of plants such as shoot, leaf, flower, blossom and root, whereby for example ears, head, spike, tassels, leaves, needles, stems, branches, blossoms, fruiting bodies, fruits and seed as well as roots, corms and rhizomes are listed.

In a particular embodiment the plant material to be treated are leaves, shoots, flowers, grains, seeds, head, spikes.

In a particular embodiment the plant material to be treated are leaves, shoots, spikes, heads, grains, seeds.

By 'plant propagation material' is meant generative and vegetative parts of a plant including seeds of all kinds (fruit, tubers, bulbs, grains etc), runners, pods, fruiting bodies, roots, rhizomes, cuttings, corms, cut shoots and the like.

Plant propagation material may also include plants and young plants which are to be transplanted after germination or after emergence from the soil.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

In a particular embodiment crops from the family of Poaceae which is comprised of wheat, oat, barley, rye, triticale, millet, corn, maize can be protected by the method of the invention.

In a very particular embodiment wheat, oat, barley, rye, triticale can be protected by the method of the invention.

The methods, Pydiflumetofen and compositions comprising Pydiflumetofen are suitable for reducing mycotoxin contamination on a number of plants and their propagation material including, but not limited to the following target crops: vine, flaxcotton, cereals (wheat, barley, rye, oats, millet, triticale, maize (including field corn, pop corn and sweet corn), rice, sorghum and related crops); beet (sugar beet and fodder beet); sugar beet, sugar cane, leguminous plants (beans, lentils, peas, soybeans); oil plants (rape, mustard, sunflowers), *Brassica* oilseeds such as *Brassica napus* (e.g. canola), *Brassica rapa, B. juncea* (e.g. mustard) and *Brassica carinata*; cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.)); various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of Pydiflumetofen and compositions comprising Pydiflumetofen, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, Pydiflumetofen and compositions comprising Pydiflumetofen may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with Pydiflumetofen and compositions comprising Pydiflumetofen.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means.

For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a *Petunia* EPSPS, a Tomato EPSPS, or an *Eleusine* EPSPS (WO 2001/66704). It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the abovementioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described. Other imidazolinone-tolerant plants are also described. Further sulfonylurea- and imidazolinone-tolerant plants are also described.

Other plants tolerant to imidazolinone and/or sulfonylurea can be obtained by induced mutagenesis, selection in cell cultures in the presence of the herbicide or mutation breeding as described for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or
3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034; or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;
5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants.
b. plants which contain a stress tolerance enhancing transgene capable of reducing the expression and/or the activity of the PARG encoding genes of the plants or plants cells.
c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed.
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alternan,
3) transgenic plants which produce hyaluronan.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes,
b) Plants, such as cotton plants, containing an altered form of rsw2 or rsw3 homologous nucleic acids,
c) Plants, such as cotton plants, with increased expression of sucrose phosphate synthase,
d) Plants, such as cotton plants, with increased expression of sucrose synthase,
e) Plants, such as cotton plants, wherein the timing of the plasmodesmatal gating at the basis of the fiber cell is altered, e.g. through downregulation of fiberselective β1,3-glucanase,
f) Plants, such as cotton plants, having fibers with altered reactivity, e.g. through the expression of N-acteylglucosaminetransferase gene including nodC and chitinsynthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content,
b) Plants such as oilseed rape plants, producing oil having a low linolenic acid content,
c) Plant such as oilseed rape plants, producing oil having a low level of saturated fatty acids.

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

TABLE A

| No. | Transgenic event | Company | Description | Crop |
|---|---|---|---|---|
| A-1 | ASR368 | Scotts Seeds | Glyphosate tolerance derived by inserting a modified 5-enolpyruvylshikimate-3-phosphate synthase (EPSPS) encoding gene from *Agrobacterium tumefaciens.* | *Agrostis stolonifera* Creeping Bentgrass |

TABLE A-continued

| No. | Trans-genic event | Company | Description | Crop |
|---|---|---|---|---|
| A-2 | H7-1 | Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. | *Beta vulgaris* |
| A-3 | T120-7 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Beta vulgaris* |
| A-4 | GTSB77 | Novartis Seeds; Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. | *Beta vulgaris* sugar Beet |
| A-5 | 23-18-17, 23-198 | Monsanto Company (formerly Calgene) | High laurate (12:0) and myristate (14:0) canola produced by inserting a thioesterase encoding gene from the California bay laurel (*Umbellularia californica*). | *Brassica napus* (Argentine Canola) |
| A-6 | 45A37, 46A40 | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. | *Brassica napus* (Argentine Canola) |
| A-7 | 46A12, 46A16 | Pioneer Hi-Bred International Inc. | Combination of chemical mutagenesis, to achieve the high oleic acid trait, and traditional breeding with registered canola varieties. | *Brassica napus* (Argentine Canola) |
| A-8 | GT200 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) |
| A-9 | GT73, RT73 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) |
| A-10 | HCN10 | Aventis CropScience | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| A-11 | HCN92 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| A-12 | MS1, RF1 => PGS1 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| A-13 | MS1, RF2 => PGS2 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| A-14 | MS8 × RF3 | Bayer CropScience (Aventis CropScience(AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| A-15 | NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. | *Brassica napus* (Argentine Canola) |
| A-16 | OXY-235 | Aventis CropScience (formerly Rhône Poulenc Inc.) | Tolerance to the herbicides bromoxynil and ioxynil by incorporation of the nitrilase gene from *Klebsiella pneumoniae*. | *Brassica napus* (Argentine Canola) |
| A-17 | PHY14, PHY35 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. | *Brassica napus* (Argentine Canola) |
| A-18 | PHY36 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. | *Brassica napus* (Argentine Canola) |
| A-19 | T45 (HCN28) | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| A-20 | HCR-1 | Bayer CropScience (Aventis CropScience(AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. | *Brassica rapa* (Polish Canola) |

TABLE A-continued

| No. | Trans-genic event | Company | Description | Crop |
|---|---|---|---|---|
| A-21 | ZSR500/502 | Monsanto Company | Introduction of a modified 5-enol-pyruvylshikimate-3-phosphate synthase (EPSPS) and a gene from *Achromobacter* sp that degrades glyphosate by conversion to aminomethylphosphonic acid (AMPA) and glyoxylate by interspecific crossing with GT73. | *Brassica rapa* (Polish Canola) |
| A-22 | 55-1/63-1 | Cornell University | Papaya ringspot virus (PRSV) resistant papaya produced by inserting the coat protein (CP) encoding sequences from this plant potyvirus. | *Carica papaya* (Papaya) |
| A-23 | RM3-3, RM3-4, RM3-6 | Bejo Zaden BV | Male sterility was via insertion of the barnase ribonuclease gene from *Bacillus amyloliquefaciens*; PPT resistance was via the bar gene from *S. hygroscopicus*, which encodes the PAT enzyme. | *Cichorium intybus* (Chicory) |
| A-24 | A, B | Agritope Inc. | Reduced accumulation of S-adenosylmethionine (SAM), and consequently reduced ethylene synthesis, by introduction of the gene encoding S-adenosylmethionine hydrolase. | *Cucumis melo* (Melon) |
| A-25 | CZW-3 | Asgrow (USA); Seminis Vegetable Inc. (Canada) | Cucumber mosiac virus (CMV), zucchini yellows mosaic (ZYMV) and watermelon mosaic virus (WMV) 2 resistant squash (*Curcurbita pepo*) produced by inserting the coat protein (CP) encoding sequences from each of these plant viruses into the host genome. | *Cucurbita pepo* (Squash) |
| A-26 | ZW20 | Upjohn (USA); Seminis Vegetable Inc. (Canada) | Zucchini yellows mosaic (ZYMV) and watermelon mosaic virus (WMV) 2 resistant squash (*Curcurbita pepo*) produced by inserting the coat protein (CP) encoding sequences from each of these plant potyviruses into the host genome. | *Cucurbita pepo* (Squash) |
| A-27 | 66 | Florigene Pty Ltd. | Delayed senescence and sulfonylurea herbicide tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulfonyl urea herbicides was via the introduction of a chlorsulfuron tolerant version of the acetolactate synthase (ALS) encoding gene from tobacco. | *Dianthus caryophyllus* (Carnation) |
| A-28 | 4, 11, 15, 16 | Florigene Pty Ltd. | Modified colour and sulfonylurea herbicide tolerant carnations produced by inserting two anthocyanin biosynthetic genes whose expression results in a violet/mauve colouration. Tolerance to sulfonyl urea herbicides was via the introduction of a chlorsulfuron tolerant version of the acetolactate synthase (ALS) encoding gene from tobacco. | *Dianthus caryophyllus* (Carnation) |
| A-29 | 959A, 988A, 1226A, 1351A, 1363A, 1400A | Florigene Pty Ltd. | Introduction of two anthocyanin biosynthetic genes to result in a violet/mauve colouration; Introduction of a variant form of acetolactate synthase (ALS). | *Dianthus caryophyllus* (Carnation) |
| A-30 | A2704-12, A2704-21, A5547-35 | Aventis CropScience | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| A-31 | A5547-127 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| A-32 | DP356043 | Pioneer Hi-Bred International Inc. | Soybean event with two herbicide tolerance genes: glyphosate N-acetlytransferase, which detoxifies glyphosate, and a modified acetolactate synthase (A | *Glycine max* L. (Soybean) |
| A-33 | G94-1, G94-19, G168 | DuPont Canada Agricultural Products | High oleic acid soybean produced by inserting a second copy of the fatty acid desaturase (GmFad2-1) encoding gene from soybean, which resulted in “silencing” of the endogenous host gene. | *Glycine max* L. (Soybean) |
| A-34 | GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. | *Glycine max* L. (Soybean) |
| A-35 | GU262 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| A-36 | MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4. | *Glycine max* L. (Soybean) |
| A-37 | OT96-15 | Agriculture & Agri-Food Canada | Low linolenic acid soybean produced through traditional cross-breeding to incorporate the novel trait from a naturally occurring fan1 gene mutant that was selected for low linolenic acid. | *Glycine max* L. (Soybean) |
| A-38 | W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus*. | *Glycine max* L. (Soybean) |
| A-39 | 15985 | Monsanto Company | Insect resistant cotton derived by transformation of the DP50B parent variety, which contained event 531 (expressing Cry1Ac protein), with purified plasmid DNA containing the cry2Ab gene from *B. thuringiensis* subsp. *kurstaki*. | *Gossypium hirsutum* L. (Cotton) |
| A-40 | 19-51A | DuPont Canada Agricultural Products | Introduction of a variant form of acetolactate synthase (ALS). | *Gossypium hirsutum* L. (Cotton) |
| A-41 | 281-24-236 | DOW AgroSciences LLC | Insect-resistant cotton produced by inserting the cry1F gene from *Bacillus thuringiensis* var. *aizawai*. The PAT encoding gene from *Streptomyces viridochromogenes* was introduced as a selectable marker. | *Gossypium hirsutum* L. (Cotton) |

TABLE A-continued

| No. | Trans-genic event | Company | Description | Crop |
|---|---|---|---|---|
| A-42 | 3006-210-23 | DOW AgroSciences LLC | Insect-resistant cotton produced by inserting the cry1Ac gene from *Bacillus thuringiensis* subsp. *kurstaki*. The PAT encoding gene from *Streptomyces viridochromogenes* was introduced as a selectable marker. | *Gossypium hirsutum* L. (Cotton) |
| A-43 | 31807/31808 | Calgene Inc. | Insect-resistant and bromoxynil herbicide tolerant cotton produced by inserting the cry1Ac gene from *Bacillus thuringiensis* and a nitrilase encoding gene from *Klebsiella pneumoniae*. | *Gossypium hirsutum* L. (Cotton) |
| A-44 | BXN | Calgene Inc. | Bromoxynil herbicide tolerant cotton produced by inserting a nitrilase encoding gene from *Klebsiella pneumoniae*. | *Gossypium hirsutum* L. (Cotton) |
| A-45 | COT102 | Syngenta Seeds, Inc. | Insect-resistant cotton produced by inserting the vip3A(a) gene from *Bacillus thuringiensis* AB88. The APH4 encoding gene from *E. coli* was introduced as a selectable marker. | *Gossypium hirsutum* L. (Cotton) |
| A-46 | DAS-21Ø23-5 × DAS-24236-5 | DOW AgroSciences LLC | WideStrike ™, a stacked insect-resistant cotton derived from conventional cross-breeding of parental lines 3006-210-23 (OECD identifier: DAS-21Ø23-5) and 281-24-236 (OECD identifier: DAS-24236-5). | *Gossypium hirsutum* L. (Cotton) |
| A-47 | DAS-21Ø23-5 × DAS-24236-5 × MON88913 | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). | *Gossypium hirsutum* L. (Cotton) |
| A-48 | DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). | *Gossypium hirsutum* L. (Cotton) |
| A-49 | LLCotton25 | Bayer CropScience (Aventis CropScience(AgrEvo)) | Glufosinate ammonium herbicide tolerant cotton produced by inserting a modified phosphinothricin acetyltransferase (PAT) encoding gene from the soil bacterium *Streptomyces hygroscopicus*. | *Gossypium hirsutum* L. (Cotton) |
| A-50 | LLCotton25 × MON15985 | Bayer CropScience (Aventis CropScience(AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) | *Gossypium hirsutum* L. (Cotton) |
| A-51 | MON1445/1698 | Monsanto Company | Glyphosate herbicide tolerant cotton produced by inserting a naturally glyphosate tolerant form of the enzyme 5-enolpyruvyl shikimate-3-phosphate synthase (EPSPS) from *A. tumefaciens* strain CP4. | *Gossypium hirsutum* L. (Cotton) |
| A-52 | MON15985 × MON88913 | Monsanto Company | Stacked insect resistant and glyphosate tolerant cotton produced by conventional cross-breeding of the parental lines MON88913 (OECD identifier: MON-88913-8) and 15985 (OECD identifier: MON-15985-7). Glyphosate tolerance is derived from MON88913 which contains two genes encoding the enzyme 5-enolypyruvylshikimate-3-phosphate synthase (EPSPS) from the CP4 strain of *Agrobacterium tumefaciens*. Insect resistance is derived MON15985 which was produced by transformation of the DP50B parent variety, which contained event 531 (expressing Cry1Ac protein), with purified plasmid DNA containing the cry2Ab gene from *B. thuringiensis* subsp. *kurstaki*. | *Gossypium hirsutum* L. (Cotton) |
| A-53 | MON-15985-7 × MON-Ø1445-2 | Monsanto Company | Stacked insect resistant and herbicide tolerant cotton derived from conventional cross-breeding of the parental lines 15985 (OECD identifier: MON-15985-7) and MON1445 (OECD identifier: MON-Ø1445-2). | *Gossypium hirsutum* L. (Cotton) |
| A-54 | MON531/757/1076 | Monsanto Company | Insect-resistant cotton produced by inserting the cry1Ac gene from *Bacillus thuringiensis* subsp. *kurstaki* HD-73 (B.t.k.). | *Gossypium hirsutum* L. (Cotton) |
| A-55 | MON88913 | Monsanto Company | Glyphosate herbicide tolerant cotton produced by inserting two genes encoding the enzyme 5-enolypyruvylshikimate-3-phosphate synthase (EPSPS) from the CP4 strain of *Agrobacterium tumefaciens*. | *Gossypium hirsutum* L. (Cotton) |
| A-56 | MON-ØØ531-6 × MON-Ø1445-2 | Monsanto Company | Stacked insect resistant and herbicide tolerant cotton derived from conventional cross-breeding of the parental lines MON531 (OECD identifier: MON-ØØ531-6) and MON1445 (OECD identifier: MON-Ø1445-2). | *Gossypium hirsutum* L. (Cotton) |
| A-57 | X81359 | BASF Inc. | Tolerance to imidazolinone herbicides by selection of a naturally occurring mutant. | *Helianthus annuus* (Sunflower) |
| A-58 | RH44 | BASF Inc. | Selection for a mutagenized version of the enzyme acetohydroxyacid synthase (AHAS), also known as acetolactate synthase (ALS) or acetolactate pyruvate-lyase. | *Lens culinaris* (Lentil) |
| A-59 | FP967 | University of Saskatchewan, Crop Dev. Centre | A variant form of acetolactate synthase (ALS) was obtained from a chlorsulfuron tolerant line of *A. thaliana* and used to transform flax. | *Linum usitatissimum* L. (Flax, Linseed) |
| A-60 | 5345 | Monsanto Company | Resistance to lepidopteran pests through the introduction of the cry1Ac gene from *Bacillus thuringiensis* subsp. *Kurstaki*. | *Lycopersicon esculentum* (Tomato) |

TABLE A-continued

| No. | Trans-genic event | Company | Description | Crop |
|---|---|---|---|---|
| A-61 | 8338 | Monsanto Company | Introduction of a gene sequence encoding the enzyme 1-amino-cyclopropane-1-carboxylic acid deaminase (ACCd) that metabolizes the precursor of the fruit ripening hormone ethylene. | *Lycopersicon esculentum* (Tomato) |
| A-62 | 1345-4 | DNA Plant Technology Corporation | Delayed ripening tomatoes produced by inserting an additional copy of a truncated gene encoding 1-aminocyclopropane-1-carboxyllic acid (ACC) synthase, which resulted in downregulation of the endogenous ACC synthase and reduced ethylene accumulation. | *Lycopersicon esculentum* (Tomato) |
| A-63 | 35 1 N | Agritope Inc. | Introduction of a gene sequence encoding the enzyme S-adenosylmethionine hydrolase that metabolizes the precursor of the fruit ripening hormone ethylene | *Lycopersicon esculentum* (Tomato) |
| A-64 | B, Da, F | Zeneca Seeds | Delayed softening tomatoes produced by inserting a truncated version of the polygalacturonase (PG) encoding gene in the sense or anti-sense orientation in order to reduce expression of the endogenous PG gene, and thus reduce pectin degradation. | *Lycopersicon esculentum* (Tomato) |
| A-65 | FLAVR SAVR | Calgene Inc. | Delayed softening tomatoes produced by inserting an additional copy of the polygalacturonase (PG) encoding gene in the anti-sense orientation in order to reduce expression of the endogenous PG gene and thus reduce pectin degradation. | *Lycopersicon esculentum* (Tomato) |
| A-66 | J101, J163 | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. | *Medicago sativa* (Alfalfa) |
| A-67 | C/F/93/08-02 | Societe National d'Exploitation des Tabacs et Allumettes | Tolerance to the herbicides bromoxynil and ioxynil by incorporation of the nitrilase gene from *Klebsiella pneumoniae*. | *Nicotiana tabacum* L. (Tobacco) |
| A-68 | Vector 21-41 | Vector Tobacco Inc. | Reduced nicotine content through introduction of a second copy of the tobacco quinolinic acid phosphoribosyltransferase (QTPase) in the antisense orientation. The NPTII encoding gene from *E. coli* was introduced as a selectable marker to identify transformants. | *Nicotiana tabacum* L. (Tobacco) |
| A-69 | CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) |
| A-70 | IMINTA-1, IMINTA-4 | BASF Inc. | Tolerance to imidazolinone herbicides induced by chemical mutagenesis of the acetolactate synthase (ALS) enzyme using sodium azide. | *Oryza sativa* (Rice) |
| A-71 | LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*). | *Oryza sativa* (Rice) |
| A-72 | LLRICE601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*). | *Oryza sativa* (Rice) |
| A-73 | C5 | United States Department of Agriculture - Agricultural Research Service | Plum pox virus (PPV) resistant plum tree produced through *Agrobacterium*-mediated transformation with a coat protein (CP) gene from the virus. | *Prunus domestica* (Plum) |
| A-74 | PWC16 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) |
| A-75 | ATBT04-6, ATBT04-27, ATBT04-30, ATBT04-31, ATBT04-36, SPBT02-5, SPBT02-7 | Monsanto Company | Colorado potato beetle resistant potatoes produced by inserting the cry3A gene from *Bacillus thuringiensis* (subsp. *Tenebrionis*). | *Solanum tuberosum* L. (Potato) |
| A-76 | BT6, BT10, BT12, BT16, BT17, BT18, BT23 | Monsanto Company | Colorado potato beetle resistant potatoes produced by inserting the cry3A gene from *Bacillus thuringiensis* (subsp. *Tenebrionis*). | *Solanum tuberosum* L. (Potato) |
| A-77 | RBMT15-101, SEMT15-02, SEMT15-15 | Monsanto Company | Colorado potato beetle and potato virus Y (PVY) resistant potatoes produced by inserting the cry3A gene from *Bacillus thuringiensis* (subsp. *Tenebrionis*) and the coat protein encoding gene from PVY. | *Solanum tuberosum* L. (Potato) |

TABLE A-continued

| No. | Trans-genic event | Company | Description | Crop |
|---|---|---|---|---|
| A-78 | RBMT21-129, RBMT21-350, RBMT22-082 | Monsanto Company | Colorado potato beetle and potato leafroll virus (PLRV) resistant potatoes produced by inserting the cry3A gene from *Bacillus thuringiensis* (subsp. *Tenebrionis*) and the replicase encoding gene from PLRV. | *Solanum tuberosum* L. (Potato) |
| A-79 | AP205CL | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| A-80 | AP602CL | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| A-81 | BW255-2, BW238-3 | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| A-82 | BW7 | BASF Inc. | Tolerance to imidazolinone herbicides induced by chemical mutagenesis of the acetohydroxyacid synthase (AHAS) gene using sodium azide. | *Triticum aestivum* (Wheat) |
| A-83 | MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. | *Triticum aestivum* (Wheat) |
| A-84 | SWP965001 | Cyanamid Crop Protection | Selection for a mutagenized version of the enzyme acetohydroxyacid synthase (AHAS), also known as acetolactate synthase (ALS) or acetolactate pyruvate-lyase. | *Triticum aestivum* (Wheat) |
| A-85 | Teal 11A | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| A-86 | 176 | Syngenta Seeds, Inc. | Insect-resistant maize produced by inserting the cry1Ab gene from *Bacillus thuringiensis* subsp. *kurstaki*. The genetic modification affords resistance to attack by the European corn borer (ECB). | *Zea mays* L. (Maize) |
| A-87 | 3751IR | Pioneer Hi-Bred International Inc. | Selection of somaclonal variants by culture of embryos on imidazolinone containing media. | *Zea mays* L. (Maize) |
| A-88 | 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. | *Zea mays* L. (Maize) |
| A-89 | ACS-ZMØØ3-2 × MON-ØØ81Ø-6 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). | *Zea mays* L. (Maize) |
| A-90 | B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. | *Zea mays* L. (Maize) |
| A-91 | BT11 (X4334CBR, X4734CBR) | Syngenta Seeds, Inc. | Insect-resistant and herbicide tolerant maize produced by inserting the cry1Ab gene from *Bacillus thuringiensis* subsp. *kurstaki*, and the phosphinothricin N-acetyltransferase (PAT) encoding gene from *S. viridochromogenes*. | *Zea mays* L. (Maize) |
| A-92 | BT11 × MIR604 | Syngenta Seeds, Inc. | Stacked insect resistant and herbicide tolerant maize produced by conventional cross breeding of parental lines BT11 (OECD unique identifier: SYN-BTØ11-1) and MIR604 (OECD unique identifier: SYN-IR6Ø5-5). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. | *Zea mays* L. (Maize) |
| A-93 | BT11 × MIR604 × GA21 | Syngenta Seeds, Inc. | Stacked insect resistant and herbicide tolerant maize produced by conventional cross breeding of parental lines BT11 (OECD unique identifier: SYN-BTØ11-1), MIR604 (OECD unique identifier: SYN-IR6Ø5-5) and GA21 (OECD unique identifier: MON-ØØØ21-9). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. Tolerance to glyphosate herbcicide is derived from GA21 which contains a a modified EPSPS gene from maize. | *Zea mays* L. (Maize) |
| A-94 | CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. | *Zea mays* L. (Maize) |
| A-95 | DAS-06275-8 | DOW AgroSciences LLC | Lepidopteran insect resistant and glufosinate ammonium herbicide-tolerant maize variety produced by inserting the cry1F gene from *Bacillus thuringiensis* var *aizawai* and the phosphinothricin acetyltransferase (PAT) from *Streptomyces hygroscopicus*. | *Zea mays* L. (Maize) |
| A-96 | DAS-59122-7 | DOW AgroSciences LLC and Pioneer Hi-Bred | Corn rootworm-resistant maize produced by inserting the cry34Ab1 and cry35Ab1 genes from *Bacillus thuringiensis* strain PS149B1. The PAT | *Zea mays* L. (Maize) |

TABLE A-continued

| No. | Trans-genic event | Company | Description | Crop |
|---|---|---|---|---|
| | | International Inc. | encoding gene from *Streptomyces viridochromogenes* was introduced as a selectable marker. | |
| A-97 | DAS-59122-7 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Tolerance to glyphosate herbcicide is derived from NK603. | *Zea mays* L. (Maize) |
| A-98 | DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-Ø15Ø7-1) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Lepidopteran resistance and toleraance to glufosinate ammonium herbicide is derived from TC1507. Tolerance to glyphosate herbcicide is derived from NK603. | *Zea mays* L. (Maize) |
| A-99 | DAS-Ø15Ø7-1 × MON-ØØ6Ø3-6 | DOW AgroSciences LLC | Stacked insect resistant and herbicide tolerant corn hybrid derived from conventional cross-breeding of the parental lines 1507 (OECD identifier: DAS-Ø15Ø7-1) and NK603 (OECD identifier: MON-ØØ6Ø3-6). | *Zea mays* L. (Maize) |
| A-100 | DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* | *Zea mays* L. (Maize) |
| A-101 | DK404SR | BASF Inc. | Somaclonal variants with a modified acetyl-CoA-carboxylase (ACCase) were selected by culture of embryos on sethoxydim enriched medium. | *Zea mays* L. (Maize) |
| A-102 | Event 3272 | Syngenta Seeds, Inc. | Maize line expressing a heat stable alpha-amylase gene amy797E for use in the dry-grind ethanol process. The phosphomannose isomerase gene from *E. coli* was used as a selectable marker. | *Zea mays* L. (Maize) |
| A-103 | EXP1910 IT | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). | *Zea mays* L. (Maize) |
| A-104 | GA21 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | *Zea mays* L. (Maize) |
| A-105 | IT | Pioneer Hi-Bred International Inc. | Tolerance to the imidazolinone herbicide, imazethapyr, was obtained by in vitro selection of somaclonal variants. | *Zea mays* L. (Maize) |
| A-106 | LY038 | Monsanto Company | Altered amino acid composition, specifically elevated levels of lysine, through the introduction of the cordapA gene, derived from *Corynebacterium glutamicum*, encoding the enzyme dihydrodipicolinate synthase (cDHDPS). | *Zea mays* L. (Maize) |
| A-107 | MIR604 | Syngenta Seeds, Inc. | Corn rootworm resistant maize produced by transformation with a modified cry3A gene. The phosphomannose isomerase gene from *E. coli* was used as a selectable marker. | *Zea mays* L. (Maize) |
| A-108 | MIR604 × GA21 | Syngenta Seeds, Inc. | Stacked insect resistant and herbicide tolerant maize produced by conventional cross breeding of parental lines MIR604 (OECD unique identifier: SYN-IR6Ø5-5) and GA21 (OECD unique identifier: MON-ØØØ21-9). Corn rootworm-resistance is derived from MIR604 which contains the mcry3A gene from *Bacillus thuringiensis*. Tolerance to glyphosate herbcicide is derived from GA21. | *Zea mays* L. (Maize) |
| A-109 | MON80100 | Monsanto Company | Insect-resistant maize produced by inserting the cry1Ab gene from *Bacillus thuringiensis* subsp. *kurstaki*. The genetic modification affords resistance to attack by the European corn borer (ECB). | *Zea mays* L. (Maize) |
| A-110 | MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. | *Zea mays* L. (Maize) |
| A-111 | MON809 | Pioneer Hi-Bred International Inc. | Resistance to European corn borer (*Ostrinia nubilalis*) by introduction of a synthetic cry1Ab gene. Glyphosate resistance via introduction of the bacterial version of a plant enzyme, 5-enolpyruvyl shikimate-3-phosphate synthase (EPSPS). | *Zea mays* L. (Maize) |
| A-112 | MON810 | Monsanto Company | Insect-resistant maize produced by inserting a truncated form of the cry1Ab gene from *Bacillus thuringiensis* subsp. *kurstaki* HD-1. The genetic modification affords resistance to attack by the European corn borer (ECB). | *Zea mays* L. (Maize) |
| A-113 | MON810 × MON88017 | Monsanto Company | Stacked insect resistant and glyphosate tolerant maize derived from conventional cross-breeding of the parental lines MON810 (OECD identifier: MON-ØØ81Ø-6) and MON88017 (OECD identifier: MON-88Ø17-3). European corn borer (ECB) resistance is derived from a truncated form of the cry1Ab gene from *Bacillus thuringiensis* subsp. *kurstaki* HD-1 present in MON810. Corn rootworm resistance is derived from the cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. | *Zea mays* L. (Maize) |
| A-114 | MON832 | Monsanto Company | Introduction, by particle bombardment, of glyphosate oxidase (GOX) and a modified 5-enolpyruvyl shikimate-3-phosphate synthase (EPSPS), an enzyme | *Zea mays* L. (Maize) |

TABLE A-continued

| No. | Trans-genic event | Company | Description | Crop |
|---|---|---|---|---|
| | | | involved in the shikimate biochemical pathway for the production of the aromatic amino acids. | |
| A-115 | MON863 | Monsanto Company | Corn root worm resistant maize produced by inserting the cry3Bb1 gene from *Bacillus thuringiensis* subsp. *kumamotoensis*. | *Zea mays* L. (Maize) |
| A-116 | MON88017 | Monsanto Company | Corn rootworm-resistant maize produced by inserting the cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4. | *Zea mays* L. (Maize) |
| A-117 | MON89034 | Monsanto Company | Maize event expressing two different insecticidal proteins from *Bacillus thuringiensis* providing resistance to number of lepidopteran pests. | *Zea mays* L. (Maize) |
| A-118 | MON89034 × MON88017 | Monsanto Company | Stacked insect resistant and glyphosate tolerant maize derived from conventional cross-breeding of the parental lines MON89034 (OECD identifier: MON-89Ø34-3) and MON88017 (OECD identifier: MON-88Ø17-3). Resistance to Lepiopteran insects is derived from two crygenes present in MON89043. Corn rootworm resistance is derived from a single cry genes and glyphosate tolerance is derived from the 5-enolpyruvylshikimate-3-phosphate synthase (EPSPS) encoding gene from *Agrobacterium tumefaciens* present in MON88017. | *Zea mays* L. (Maize) |
| A-119 | MON-ØØ6Ø3-6 × MON-ØØ81Ø-6 | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). | *Zea mays* L. (Maize) |
| A-120 | MON-ØØ81Ø-6 × LY038 | Monsanto Company | Stacked insect resistant and enhanced lysine content maize derived from conventional cross-breeding of the parental lines MON810 (OECD identifier: MON-ØØ81Ø-6) and LY038 (OECD identifier: REN-ØØØ38-3). | *Zea mays* L. (Maize) |
| A-121 | MON-ØØ863-5 × MON-ØØ6Ø3-6 | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). | *Zea mays* L. (Maize) |
| A-122 | MON-ØØ863-5 × MON-ØØ81Ø-6 | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) | *Zea mays* L. (Maize) |
| A-123 | MON-ØØ863-5 × MON-ØØ81Ø-6 × MON-ØØ6Ø3-6 | Monsanto Company | Stacked insect resistant and herbicide tolerant corn hybrid derived from conventional cross-breeding of the stacked hybrid MON-ØØ863-5 × MON-ØØ81Ø-6 and NK603 (OECD identifier: MON-ØØ6Ø3-6). | *Zea mays* L. (Maize) |
| A-124 | MON-ØØØ21-9 × MON-ØØ81Ø-6 | Monsanto Company | Stacked insect resistant and herbicide tolerant corn hybrid derived from conventional cross-breeding of the parental lines GA21 (OECD identifider: MON-ØØØ21-9) and MON810 (OECD identifier: MON-ØØ81Ø-6). | *Zea mays* L. (Maize) |
| A-125 | MS3 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | *Zea mays* L. (Maize) |
| A-126 | MS6 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | *Zea mays* L. (Maize) |
| A-127 | NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | *Zea mays* L. (Maize) |
| A-128 | SYN-BTØ11-1 × MON-ØØØ21-9 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). | *Zea mays* L. (Maize) |
| A-129 | T14, T25 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. | *Zea mays* L. (Maize) |
| A-130 | TC1507 | Mycogen (c/o Dow AgroSciences); Pioneer (c/o Dupont) | Insect-resistant and glufosinate ammonium herbicide tolerant maize produced by inserting the cry1F gene from *Bacillus thuringiensis* var. *aizawai* and the phosphinothricin N-acetyltransferase encoding gene from *Streptomyces viridochromogenes*. | *Zea mays* L. (Maize) |
| A-131 | TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due the presence of the cry1F gene from *Bacillus thuringiensis* var. *aizawai*. Corn rootworm-resistance is derived from DAS-59122-7 which contains the cry34Ab1 and cry35Ab1 genes from *Bacillus thuringiensis* strain PS149B1. Tolerance to glufosinate ammonium herbcicide is derived from TC1507 from the phosphinothricin N-acetyltransferase encoding gene from *Streptomyces viridochromogenes*. | *Zea mays* L. (Maize) |
| A-132 | MON89788 | Monsanto | Glyphosate-tolerant soybean produced by inserting a modified 5-enolpyruvylshikimate-3-phosphate synthase (EPSPS) encoding aroA (epsps) gene from *Agrobacterium tumefaciens* CP4. | Soybean |

When used in the methods of the invention, Pydiflumetofen may be in unmodified form or, preferably, formulated together with carriers and adjuvants conventionally employed in the art of formulation.

The invention therefore also relates to a composition for the control of mycotoxin contamination comprising Pydiflumetofen as defined above and an agriculturally acceptable support, carrier or filler.

According to the invention, the term "support" denotes a natural or synthetic, organic or inorganic compound with which Pydiflumetofen is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when Pydiflumetofen or Pydiflumetofen in combination with other actives and/or the inert support are water-insoluble and when the vector agent for the application is water. Preferably, surfactant content may be comprised from 5% to 40% by weight of the composition.

Colouring agents such as inorganic pigments, for example iron oxide, titanium oxide, ferrocyanblue, and organic pigments such as alizarin, azo and metallophthalocyanine dyes, and trace elements such as iron, manganese, boron, copper, cobalt, molybdenum and zinc salts can be used.

Optionally, other additional components may also be included, e.g. protective colloids, adhesives, thickeners, thixotropic agents, penetration agents, stabilisers, sequestering agents. More generally, the active compounds, in particular Pydiflumetofen and compositions comprising Pydiflumetofen can be combined with any solid or liquid additive, which complies with the usual formulation techniques.

In general, the composition according to the invention may contain from 0.05 to 99% by weight of active compounds, preferably from 10 to 70% by weight.

The compounds or compositions according to the invention can be used as such, in form of their formulations or as the use forms prepared therefrom, such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

The treatment of plants and plant parts with the compounds or compositions according to the invention is carried out directly or by action on their environment, habitat or storage area by means of the normal treatment methods, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting.

These compositions include not only compositions which are ready to be applied to the plant or seed to be treated by means of a suitable device, such as a spraying or dusting device, but also concentrated commercial compositions which must be diluted before application to the crop.

The compounds or compositions according to the invention can be employed for reducing mycotoxin contamination in crop protection or in the protection of materials.

Within the composition according to the invention, bactericide compounds can be employed in crop protection for example for controlling Pseudomonadaceae, Rhizobiaceae, Enterobacteriaceae, Corynebacteriaceae and Streptomycetaceae.

The compounds or compositions according to the invention can be used to curatively or preventively reduce the mycotoxin contamination of plants or crops. Thus, according to a further aspect of the invention, there is provided a method for curatively or preventively reduce the mycotoxin contamination of comprising the use of a composition comprising a compound according to formula (I) according to the invention by application to the seed, the plant or to the fruit of the plant or to the soil in which the plant is growing or in which it is desired to grow.

Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation.

In general, the composition according to the invention may contain from 0.05 to 99% by weight of Pydiflumetofen, preferably from 10 to 70% by weight.

In general, the composition according to the invention may contain in total from 0.05 to 99% by weight of Pydiflumetofen in combination with other actives, preferably from 10 to 70% by weight.

Pydiflumetofen or compositions comprising Pydiflumetofen can be used as such, in form of their formulations or as the use forms prepared therefrom, such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

The treatment of plants and plant parts with Pydiflumetofen or compositions comprising Pydiflumetofen is carried out directly or by action on their environment, habitat or storage area by means of the normal treatment methods, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting.

These compositions include not only compositions which are ready to be applied to the plant or seed to be treated by means of a suitable device, such as a spraying or dusting device, but also concentrated commercial compositions which must be diluted before application to the crop.

Pydiflumetofen or compositions comprising Pydiflumetofen can be employed for reducing mycotoxin contamination in crop protection or in the protection of materials.

Within the composition according to the invention, bactericide compounds can be employed in crop protection for example for controlling Pseudomonadaceae, Rhizobiaceae, Enterobacteriaceae, Corynebacteriaceae and Streptomycetaceae.

Pydiflumetofen or compositions comprising Pydiflumetofen can be used to curatively or preventively reduce the mycotoxin contamination of plants or crops. Thus, according to a further aspect of the invention, there is provided a method for curatively or preventively reduce the mycotoxin contamination of comprising the use of a composition comprising a compound according to formula (I) according to the invention by application to the seed, the plant or to the fruit of the plant or to the soil in which the plant is growing or in which it is desired to grow.

Suitably, Pydiflumetofen or compositions comprising Pydiflumetofen may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation.

The invention furthermore includes a method for treating seed.

A further aspect of the present invention relates in particular to seeds (dormant, primed, pregerminated or even with emerged roots and leaves) treated with Pydiflumetofen or compositions comprising Pydiflumetofen. The inventive seeds are used in methods for protection of seeds and emerged plants from the seeds from phytopathogenic harmful fungi. In these methods, seed treated with at least one inventive active ingredient is used.

Pydiflumetofen or compositions comprising Pydiflumetofen are also suitable for the treatment of seeds and young seedlings. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which has been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests, microorganisms, weeds or abiotic stress.

Pydiflumetofen or compositions comprising Pydiflumetofen are suitable for protection of seed of any plant variety which is used in agriculture, in the greenhouse, in forests or in horticulture. More particularly, the seed is that of cereals (such as wheat, barley, rye, millet and oats), oilseed rape, maize, cotton, soybeen, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described above, the treatment of transgenic seed Pydiflumetofen or compositions comprising Pydiflumetofen is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originates from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

Pydiflumetofen or compositions comprising Pydiflumetofen can be applied directly, i.e. without containing any other components and without having been diluted. In general, it is preferable to apply the compositions to the seed in the form of a suitable formulation. Suitable formulations and methods for seed treatment are known to those skilled in the art. Pydiflumetofen or compositions comprising Pydiflumetofen can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rates of each single active ingredient is generally between 0.001 and 15 g per kilogram of seed, preferably between 0.01 and 5 g per kilogram of seed.

The present invention will now be described by way of the following non-limiting examples.

EXAMPLES

Example a Application of Pydiflumetofen on the Deoxynivalenol Content of Wheat The field trial in winter wheat was conducted in Germany in spring/summer 2015.

Seeds of the winter wheat variety "Reaper" were planted in autumn 2014. Fertilization, herbicide- and plant growth regulator applications were carried out according to the local agricultural practice. The trial was conducted with 3 fully randomized replicates. The plot size was 15 $m^2$.

The compound Pydifumetofen was sprayed on Jun. 10, 2015, at BBCH-growth stage 65 with an use rate of 75 g a.i./ha. Pydiflumetofen was applied as a 100 EC formulation adding an adjuvant. In the late evening of the same day, an inoculation with spores of *Gibberella zeae* was carried out by spray application.

After harvest, the Deoxynivalenol content of the wheat kernels was analyzed by HPLC-MS/MS.

The effect of Pydiflumetofen on the Deoxynivalenol content is shown in table 1.

TABLE 1

Impact of Pydiflumetofen on the Deoxynivalenol content of winter wheat

| Treatment | Use Rate (g a.i./ha) | Deoxynivalenol Content (ppm) |
|---|---|---|
| Untreated Control | — | 497 |
| Pydiflumetofen | 75 | 44 |

Example B: Application of Pydiflumetofen on the Deoxynivalenol Content of Wheat

Six field trials of wheat analysing Mycotoxin contamination were performed at locations in France and Germany during the season of 2016 with seed planting in spring. Pydiflumetofen was applied to wheat plants as a 100 EC formulation at a rate of 45 to 60 grams/ha. Mycotoxins were measured 67 days after application of Pydiflumetofen on 2016 Aug. 8.

Results for mycotoxin content are shown in table 2, result for severity of *Fusarium* infection are shown in table 3.

UTC: Untreated control

DON: deoxynivalenol

ZEA: zearalenone

TABLE 2

| Product(s) | Country | Rate (g a.i./ha) | DON (ppb) | ZEA (ppb) | 3- Acetyl Deoxynivalenol (ppb) | Nivalenol (ppb) |
|---|---|---|---|---|---|---|
| UTC | France | 0 | 1885 | 25 | not tested | not tested |
| Pydiflumetofen | France | 45 | 789 | | not tested | not tested |
| Pydiflumetofen | France | 60 | 920 | 11 | not tested | not tested |
| UTC | France | 0 | 3916 | 0 | 189 | not tested |
| Pydiflumetofen | France | 45 | 1170 | | 63 | not tested |
| Pydiflumetofen | France | 60 | 1068 | | <50 | not tested |
| UTC | Germany | 0 | 6694 | not tested | not tested | 126 |
| Pydiflumetofen | Germany | 45 | 4367 | not tested | not tested | 0 |
| Pydiflumetofen | Germany | 60 | 4761 | not tested | not tested | 0 |
| UTC | Germany | 0 | 16282 | 3836 | 56 | 159 |
| Pydiflumetofen | Germany | 45 | 6040 | — | 0 | 0 |
| Pydiflumetofen | Germany | 60 | 7507 | 878 | 0 | 0 |

TABLE 3

| Product(s) | Rate (g a.i./ha) | *Fusarium* head blight in % sev. after 11 to 20 days after application | *Fusarium* head blight in % sev. after 21 to 46 days after application | Yield in dt/ha |
|---|---|---|---|---|
| UTC | 0 | 13 | 35 | 80 |
| Pydiflumetofen | 45 | 42 | 51 | 112 |
| Pydiflumetofen | 60 | 52 | 64 | 111 |

The invention claimed is:

1. A method of reducing deoxynivalenol contamination in a plant consisting of applying to the plant as a foliar application an effective amount of a compound according to formula (I):

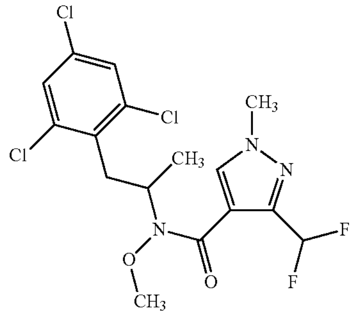

(I)

having the IUPAC name 3-(Difluoromethyl)-N-methoxy-1-methyl-N-[1-(2,4,6-trichlorophenyl)-2-propanyl]-1H-pyrazole-4-carboxamide; or a tautomer or isomer or enantiomer thereof, and a Group 1 triazole compound selected from the group consisting of cyproconazole, difenconazole, tebuconazole, metconazole, epoxiconazole, tetraconazole, and propiconazole.

2. The method according to claim 1 wherein the compound of Formula I and the Group 1 triazole are applied in a liquid composition.

3. A plant which has been treated by the method according to claim 1.

4. The method according to claim 1, wherein the plant is wheat.

5. The method according to claim 1, wherein the plant has at least 80% less deoxynivalenol contamination than a plant which has not been treated.

6. The method of claim 1, wherein the compound of formula (I) and the Group 1 triazole compound are applied during flowering.

7. A method for increasing plant yield by reducing deoxynivalenol contamination in a plant, comprising applying to the plant as a foliar application an effective amount of a compound according to formula (I):

(I)

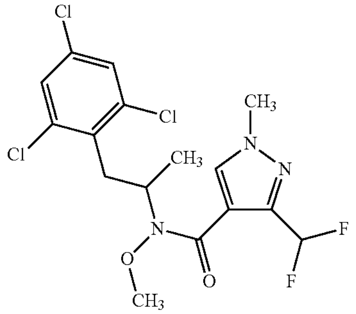

having the IUPAC name 3-(Difluoromethyl)-N-methoxy-1-methyl-N-[1-(2,4,6-trichlorophenyl)-2-propanyl]-1H-pyrazole-4-carboxamide; or a tautomer or isomer or enantiomer thereof, and a Group 1 triazole compound selected from the group consisting of cyproconazole, difenconazole, tebuconazole, metconazole, epoxiconazole, tetraconazole, and propiconazole.

8. The method according to claim 7 wherein the compound of formula (I) and the Group 1 triazole compound are applied in a liquid composition.

* * * * *